United States Patent [19]

Tomiyama

[11] Patent Number: 4,520,029

[45] Date of Patent: May 28, 1985

[54] FARNESENE DERIVATIVES, MUCOSAL STABILIZING COMPOSITIONS AND METHOD OF MANUFACTURING THE SAME

[75] Inventor: Tsuyoshi Tomiyama, Sakaki, Japan

[73] Assignee: Kotobuki Seiyaku Co., Ltd., Nagono, Japan

[21] Appl. No.: 508,142

[22] Filed: Jun. 27, 1983

Related U.S. Application Data

[63] Continuation of Ser. No. 315,464, Oct. 27, 1981, abandoned.

[30] Foreign Application Priority Data

Dec. 20, 1980 [JP] Japan .............................. 55-180833

[51] Int. Cl.$^3$ .............. C07C 125/065; C07C 103/133; A61K 31/27; A61K 31/23
[52] U.S. Cl. .................................. 514/479; 514/627; 260/404; 260/410.9 N; 560/157
[58] Field of Search ............................. 560/157, 225; 260/410.9 N, 404; 564/204, 300; 424/300, 314, 312, 320

[56] References Cited

U.S. PATENT DOCUMENTS

| | | | |
|---|---|---|---|
| 2,187,694 | 1/1940 | Slagh | 560/225 |
| 3,105,089 | 9/1963 | Kupchan | 560/225 |
| 3,584,015 | 6/1971 | Lee | 560/225 |
| 3,746,748 | 7/1973 | Ratusky | 560/225 |

OTHER PUBLICATIONS

Martindale, "The Extra Pharmacopoeia," 28th Ed., p. 80.
Cardani, J.M.C., 6, pp. 457–458, (1963).
Adami, Med. Exp., 7, pp. 171–176, (1962).
Adami, Experientia, 18, p. 461, (1962).
Shioiri, J.A.C.S., 94, pp. 6203–6205, (1972).
Allinger, "Organic Chemistry," pp. 528–530, (1971).

*Primary Examiner*—Michael L. Shippen
*Attorney, Agent, or Firm*—Robert E. Burns; Emmanuel J. Lobato; Bruce L. Adams

[57] ABSTRACT

Some new compounds, farnesyl farnesyl carboxylate, N-farnesyl farnesyl carboxamide and N-farnesyl farnesyl carbamate are disclosed, which are novel mucosal stabilizing agents showing anti-inflammative and anti-ulcerative activities. These new compounds are prepared by the reaction of farnesyl carboxylic acid with farnesol or farnesylamine.

10 Claims, No Drawings

FARNESENE DERIVATIVES, MUCOSAL STABILIZING COMPOSITIONS AND METHOD OF MANUFACTURING THE SAME

This is a continuation of application Ser. No. 315,464 filed Oct. 27, 1981, now abandoned.

BACKGROUND ART

This invention relates to a novel class of farnesene derivatives, method of manufacture therefor and new gastric mucosal stabilizing compositions. More particularly, this invention concerns farnesyl farnesyl carboxylate, N-farnesyl farnesyl carboxamide and N-farnesyl farnesyl carbamate, the methods of manufacturing the same, the use thereof gastric mucosal stabilizing agents and pharmaceutical compositions containing the new compounds.

We have been engaged in the investigation of the active component of the essential oil of Camommilla for a long time. One of our results has been open to public as U.S. Pat. No. 4,209,529.

It is well known that the main active component of the essential oil of Camomilla is guaiazulene, but a cyclic sesquiterpene, farnesene (I), has been considered to be an active component during the investigation of the essential oil of Camomilla,

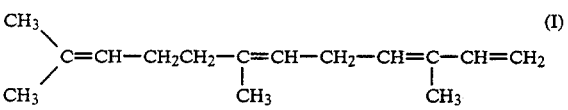

and also has been reported to possess sedative or depressive activities (Ann. Pharm. France, 33, 229 ('75)).

As a result of our studies, we have found that some new compounds obtained by coupling two farnesene groups in the form of ester, amide or carbamate, are unexpectedly less toxic and moreover, have much more excellent mucosal stabilizing, repairing and anti-inflammative activities than farnesene itself.

SUMMARY OF THE INVENTION

The principal object of the present invention is the provision of novel gastric mucosal stabilizing agents.

Another important object of the present invention is the provision of novel compounds having advantageous pharmaceutical properties.

Still another object of the present invention is to provide pharmaceutical compositions useful as mucosal stabilizing agents.

Further objects of the present invention are the provisions of pharmaceutical compositions useful as anti-inflammatory agents and a new method of treating inflammation.

Other objects of the present invention are the provisions of pharmaceutical compositions useful as anti-ulcerative agents and a new method of treating ulcer.

Further important objects of the present invention are the provisions of novel class of farnesene derivatives and methods for the manufacture thereof.

These and other objects of the invention will become evident from a consideration of the following description and claims.

DESCRIPTION OF THE INVENTION

New compounds disclosed in this invention have following general formula,

wherein A is carboxy (—COO—), carboxamide (—CONH—) or carbamoyl (—NHCOO—), 'FARNESYL' represents the following group(III)

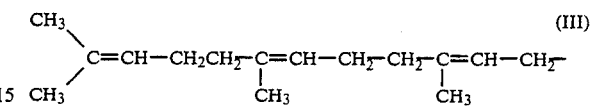

These compounds are prepared by the reaction of farnesyl carboxylic acid (IV) with farnesol or farnesyl amine.

Farnesyl carboxylic acid (IV), which is esterified with farnesol, affords the ester in the formula (V).

The usual methods are applicable to the esterification, such as the use of an acid chloride, acid anhydride or dehydrating agent (that is, DCC(dicyclohexylcarbodiimide), DPPA(diphenylphosphorylazide), Vielsmeier reagent and Mukaiyama reagent).

If, instead of farnesol, farnesylamine is reacted with farnesyl carboxylic acid the carboxamide of formula (VI) is obtained.

In this amidation, the usual procedures are applicable, the same as for esterification. Further, farnesyl carboxylic acid may take part in a Curtius rearrangement with farnesol, using a DPPA reagent, as reported by T. Shioiri et al. (Jour. Am. Chem. Soc. 94, 6203 (1972)), and gives the carbamate of formula (VII).

Farnesyl carboxylic acid used in the above reactions can be obtained by hydrolysis of farnesylbromide from bromination of farnesol (M. Julia, Bull. Soc. Chim. Fran. 1960 p1072).

In general, there exist two isomers, cis (Z) and trans (E) of compounds (V), (VI) and (VII); both isomers are included in this invention.

The compounds of the present invention are chemically stable and can be administered orally in the form of a hard or soft capsule, tablet, powder and granules with a non-toxic, pharmaceutically acceptable carrier (for example, corn starch, crystal cellulose, dextrin and cyclodextrin). Additionally, by using liquid carrier such as an edible oil, emulsifier and suspension, the compounds of the invention may be given parenterally.

When the new compounds of the invention are used for the treatment of peptic ulcer as a mucosal stabilizing agent, and for the treatment of inflammation as an anti-inflammatory, the therapeutically effective amount comprises about 100–1000 mg daily for an adult.

PHARMACOLOGICAL EXPERIMENT 1

Acute toxicity of the compounds of the present invention in ddY strain mice was determined by the up and down method, with observation for 24 hours. The compounds in this experiment were suspended in 1% methyl cellulose and given orally. The results obtained are shown in Table I.

TABLE I

| | $LD_{50}$ (permos) (mg/kg · body weight) |
|---|---|
| Compound (V) | 24500 |
| Compound (VI) | 18712 |
| Compound (VII) | 20205 |

PHARMACOLOGICAL EXPERIMENT 2

The investigation of the gastric epithelial cell stabilizing effects of these compounds were examined in rats. Male Donryu strain rats, weighing about 200 g, were given the test compound orally three times a day for five days. On the fifth day the animals were fasted for 24 hours, and submitted to pylorus ligation under light ether anesthesia. The test compounds were given just after pylorus ligation orally. After 8 hours of ligation, the rats were sacrificed and the volume of gastric juice was measured. After centrifuging 6 ml of this gastric juice at 5000 r.p.m., 2 ml of the resulting supernatant was submitted to N-acetyl neuraminic acid (NANA) determination according to the method of D. Aminoff (D. Aminoff et al., Biochem. J. 181, 384–392 (1961)). NANA content (μg/ml) in gastric juice is shown in Table 2.

TABLE 2

| Amounts of NANA | Control | Compound V | Compound VI | Compound VII |
|---|---|---|---|---|
| free | 22.5 | 17.6* | 18.3* | 16.7* |
| bound | 93.3 | 74.5* | 87.4 | 81.3 |
| total | 115.8 | 92.1* | 105.7 | 98.3 |

*significantly different from control ($P < 0.05$)

As shown in Table 2, significant reduction of NANA was observed and these findings indicate that these compounds reduce the turnover rate of gastric mucosal cell, stabilize the lysozomal membrane with increasing the ability of mucosal cell synthesis and prevent back diffusion as postulated by D. V. Parke (North American Symposium on Carbenoxolone Montreal 16p., 1976).

PHARMACOLOGICAL EXPERIMENT 3

The anti-inflammatory effect of these compounds on carragenin-induced rat paw edema was examined in accordance with the method of C. A. Winter (J. Pharmacol. 141, 369, (1936). The compounds of the present invention were suspended in 1% methyl-cellulose and orally administered at a dose of 300 mg/kg to Wister rat, weighing about 140 g. The maximum percentage inhibition during 4 hours after administration was calculated as follows:

$$\% \text{ inhibition} = \frac{\left(\begin{array}{c}\text{Paw-volume of} \\ \text{control group}\end{array}\right) - \left(\begin{array}{c}\text{paw-volume of} \\ \text{test group}\end{array}\right)}{\text{Paw-volume of control group}} \times 100$$

The results are shown in Table 3.

TABLE 3

| | Maximum inhibition (%) |
|---|---|
| Compound V | 35.8 |
| Compound VI | 30.1 |
| Compound VII | 23.7 |

As seen in Table 3, these compounds have an anti-inflammatory activity.

PHARMACOLOGICAL EXPERIMENT 4

To study the anti-ulcerative actions of these compounds of the present invention further, the stress ulcer was selected. Male Wister rats, weighing 200–250 g were subjected to stress according to Takagi et al. (Chem. Pharm. Bull 12, 465, 1964). These compounds were suspended in 1% methyl cellulose and were administered to the rat at a dose of 100 mg/kg body weight per os, 30 minutes before the stress. After stressing for 18 hours, the animals were killed by a blow on the head. The removed stomach was filled with 1% formalin solution, placed in 1% formalin solution for 15 minutes and was then cut open along the greater curvature and examined for lesion to obtain the ulcer index. The ulcer index was determined in six grades (0–5; 5 implying perforation of stomach). The results are shown in the following Table 4.

TABLE 4

| | Score |
|---|---|
| Control | 4.6 ± 0.70 |
| Compound V | 1.8 ± 0.50 |
| Compound VI | 2.3 ± 0.72 |
| Compound VII | 2.1 ± 0.41 |

As shown in Table 4, these compounds, in a dose of 100 mg/kg, inhibit the stress ulcer.

EXAMPLE 1

Farnesyl farnesyl carboxylate (Compound V)

A mixture of farnesyl carboxylic acid (5.0 g), farnesol (4.44 g) and triethylamine (4.85 g) was added dropwise at room temperature to a stirred solution of 2-chloro-1-methylpyridinium iodide (5.61 g) in 40 ml of toluene. After complete addition, the reaction mixture was heated on boiled water bath for three hours. After cooling, the mixture was washed with water and dried ($Na_2SO_4$). The solvent was removed in vacuo and gave a pale yellow oil. This material was purified by silica gel chromatography by using n-hexane and gave 7.15 g of the titled compound.

$N_D^{25} = 1.491$; $d_{23}^{25} = 0.908$.
ir; 2930, 1730, 1450, 1150 $cm^{-1}$.

EXAMPLE 2

N-Farnesyl farnesyl carboxamide (Compound VI)

To a mixture of farnesyl carboxylic acid (7.15 g) and farnesylamine (6.95 g) in 20 ml of dimethylformamide was added at 0° C. to a solution of diphenylphosphorylazide (7.62 g) in 7 ml of dimethylformamide.

Next, to this mixture was added a solution of triethylamine (3.20 g) in dimethylformamide (3 ml). The reaction mixture was kept at room temperature overnight and poured into water (900 ml). After adding table salt, this mixture was extracted with ethyl acetate. The organic phase was worked up as usual manner and gave pale yellow oil. This material was purified by silica gel chromatography by using a mixture of methanol:benzene (2:1) as the eluent and gave 11.20 g of the titled compound.

$N_D^{25} = 1.512$; $d_{23}^{25} = 0.953$.

ir: 3260, 2900, 1630, 1585, 1485 cm$^{-1}$.

EXAMPLE 3

N-Farnesyl farnesyl carbamate (Compound VII)

A mixture of farnesyl carboxylic acid (5.0 g), diphenylphosphorylazide (5.48 g) and triethylamine (2.02 g) in 45 ml of benzene was heated at reflux for 30 minutes. After 30 minutes, a solution of farnesol (4.44 g) in 10 ml of N,N-dimethylacetamide was added dropwise to the reaction mixture and heated at 80° C. for three hours. The reaction mixture was cooled, and ethyl acetate (70 ml) was added. The resulting solution was washed with water and sodium bicarbonate solution (5%). Drying (Na$_2$SO$_4$), filtration, and evaporation of solvent gave a pale yellow oil. The residue was purified by silica gel chromatography by using methanol and 6.82 g. of the titled compound was obtained.

$N_D^{25} = 1.5056$, $d_{23}^{25} = 0.9631$.

ir: 3300, 2900, 1690, 1660, 1520, 1440 cm$^{-1}$.

What we claim is:

1. The compound N-farnesyl farnesylcarboxamide of the formula: R—CONH—R, wherein R represents the group

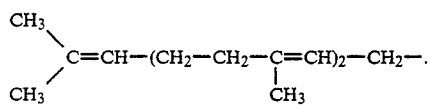

2. The compound N-farnesyl farnesylcarbamate of the formula: R—NHCOO—R, wherein R represents the group

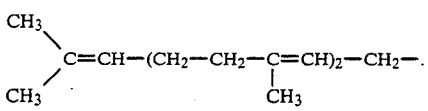

3. A therapeutic composition useful for stabilizing gastric mucosa comprising a pharmaceutically acceptable carrier and the compound defined in claim 1 in a therapeutically effective amount.

4. A therapeutic composition useful for stabilizing gastric mucosa comprising a pharmaceutically acceptable carrier and the compound defined in claim 2 in a therapeutically effective amount.

5. A method of treating peptic ulcer which comprises administering to a patient having peptic ulcer a therapeutic amount of N-farnesyl farnesylcarboxamide.

6. A method of treating peptic ulcer which comprises administering to a patient having peptic ulcer a therapeutic amount of N-farnesyl farnesylcarbamate.

7. A method of treating inflammation which comprises administering to a patient having inflammation a therapeutically effective amount of a compound selected from the group consisting of farnesyl farnesylcarboxylate, N-farnesyl farnesylcarboxamide and N-farnesyl farnesylcarbamate.

8. The method of treatment defined in claim 7, which comprises administering to a patient suffering from inflammation a therapeutically effective amount of N-farnesyl farnesylcarboxylate.

9. The method of treatment defined in claim 7, which comprises administering to a patient suffering from inflammation a therapeutically effective amount of N-farnesyl farnesylcarboxamide.

10. The method of treatment defined in claim 7, which comprises administering to a patient suffering from inflammation a therapeutically effective amount of N-farnesyl farnesylcarbamate.

* * * * *